United States Patent [19]

Buchanan

[11] Patent Number: 5,037,398
[45] Date of Patent: Aug. 6, 1991

[54] METHOD AND APPARATUS FOR RELEASABLY SECURING A PRESSURE MONITOR DEVICE

[76] Inventor: Sharon J. Buchanan, 1461 Sandy Ridge Dr., Rochester Hills, Mich. 48064

[21] Appl. No.: 432,235

[22] Filed: Nov. 6, 1989

[51] Int. Cl.$^5$ .................. A61M 25/02; A61B 5/02
[52] U.S. Cl. .................. 604/180; 128/DIG. 26; 128/DIG. 15
[58] Field of Search .......... 604/174, 178–180; 128/672, 673, 675, 692, DIG. 15, DIG. 26

[56] References Cited

U.S. PATENT DOCUMENTS

| | | | |
|---|---|---|---|
| 3,610,228 | 10/1971 | Temkin | 128/673 |
| 4,198,989 | 4/1980 | Hawke et al. | 128/675 |
| 4,248,241 | 2/1981 | Taachi | 128/685 |
| 4,416,664 | 11/1983 | Womack | 604/174 |
| 4,561,857 | 12/1985 | Sacks | 604/179 |
| 4,683,894 | 8/1987 | Kodama et al. | 128/675 |
| 4,821,736 | 4/1989 | Watson | 128/DIG. 15 |
| 4,838,878 | 6/1989 | Kalt et al. | 128/DIG. 26 |
| 4,846,807 | 7/1989 | Safadago | 128/DIG. 26 |

FOREIGN PATENT DOCUMENTS 2180944  4/1987  United Kingdom ............... 128/672

Primary Examiner—Stephen C. Pellegrino
Assistant Examiner—Ralph A. Lewis
Attorney, Agent, or Firm—Barnes, Kisselle, Raisch, Choate, Whittemore & Hulbert

[57] ABSTRACT

There is provided a fastening system for securing a pressure monitor device to a patient. The system comprises an adhesive sheet constructed and arranged to engage the base of the device, carry the device and at least one strap which folds over and releasably secures the device to the sheet and a releasable fastener which releasably secures the base of the device.

The invention aligns and secures the device against movement in lateral, vertical and axial directions to maintain the device at the level of the patient's midaxillary line.

5 Claims, 1 Drawing Sheet

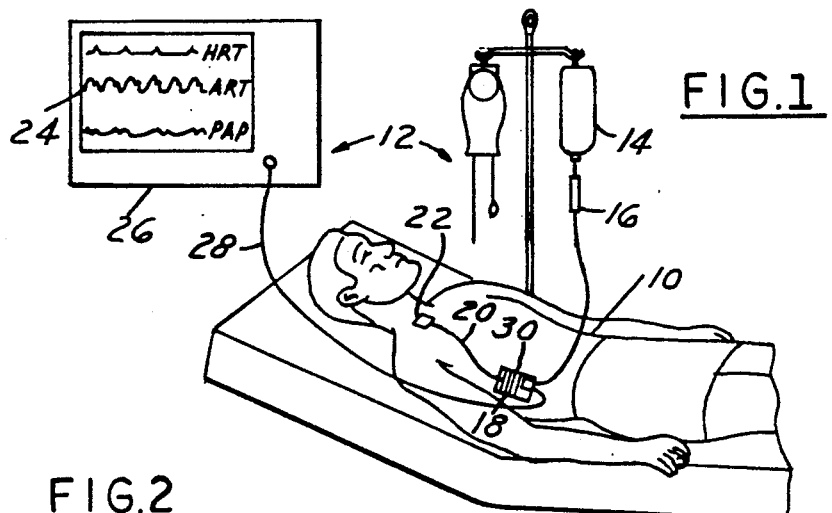
FIG.1
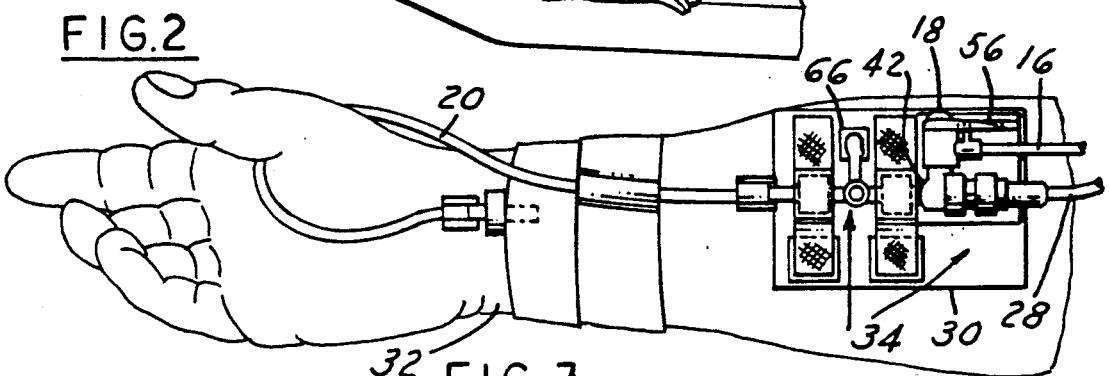
FIG.2
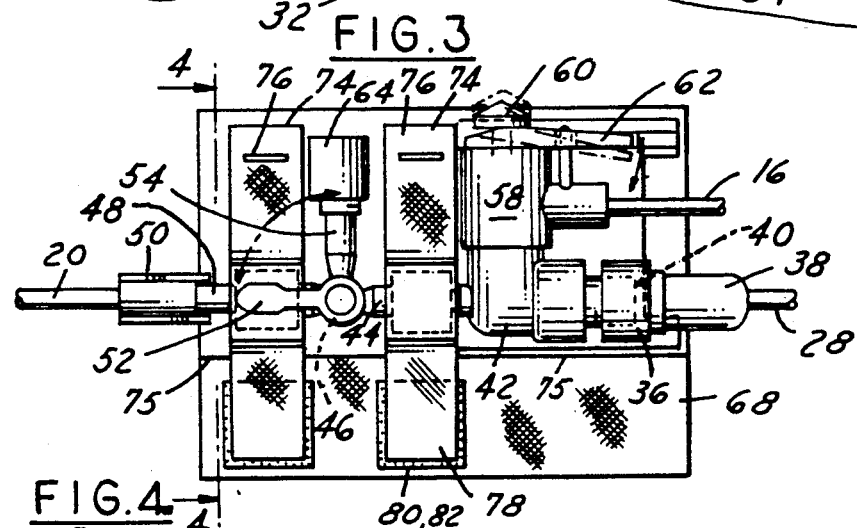
FIG.3
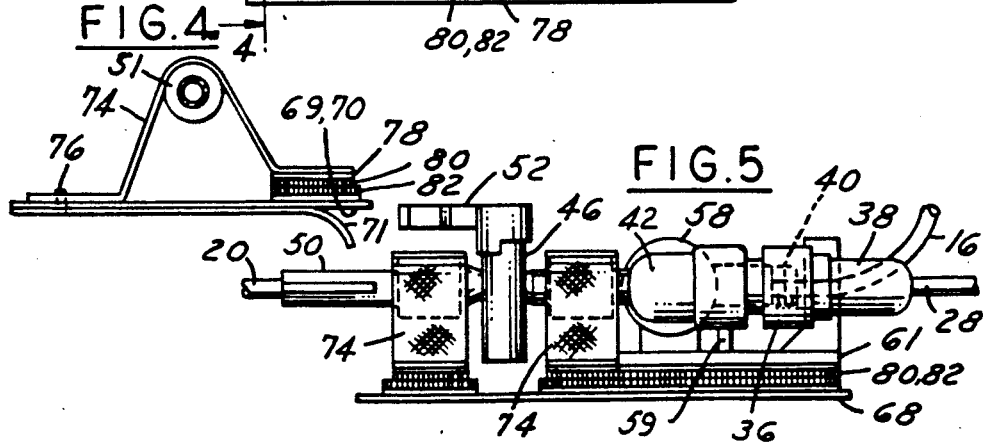
FIG.4
FIG.5

METHOD AND APPARATUS FOR RELEASABLY SECURING A PRESSURE MONITOR DEVICE

FIELD OF INVENTION

This invention relates to a method and an apparatus for releasably securing a pressure monitor device or similar device to a patient to prevent its movement.

BACKGROUND AND SUMMARY

In the medical field, tubular devices or catheters are used for insertion into canals, vessels, passageways or body cavities to permit injection, withdrawal, sampling and drainage of body fluids. Simple catheters suffice for these general uses. Currently however, more complicated devices are used for complex procedures. For example, pressure monitor devices are used to assess pulmonary artery and arterial artery functions. In order to monitor such functions, a special Swan-Gantz catheter, known as a pulmonary artery catheter, is fed into the patient's pulmonary artery where the free end is exposed to the pressure in the pulmonary artery. The other end of the catheter is connected to a pressure monitor which is secured to the patient. The pressure monitor houses a transducer which is connected to a chart recorder. The pressure monitor is an important device within a pulmonary and arterial monitoring system which begins at the free end of a catheter in the artery and ends at the chart recorder. The pressure monitors have a complex configuration and are more difficult to secure than the simple tubular devices of the past.

The prior art generally describes methods and devices for securing the simple tubular catheters to a patient to prevent dislodging of the catheter and to facilitate its attachment and removal. Thus, U.S. Pat. No. 3,288,136 discloses a method whereby a cylindrical tube or catheter is enclosed in one Velcro element and releasably secured to a surface having the other Velcro element. Lengthwise or longitudinal movement along the axis of the catheter is prevented in cooperation with a deformable sleeve compressed between the tube and the Velcro element. U.S. Pat. Nos. 3,834,380 and 3,878,849 disclose a method of releasably securing a tube in place. In U.S. Pat. No. 3,834,380, a band folds over a compressible clamping tube and folds over onto itself and is secured in the folded position by Velcro elements on the two interior surfaces of the band. An adhesive secures the band to the patient. In U.S. Pat. No. 3,878,849, a similar fold over band having Velcro mating ends is used to secure a catheter, preventing its lateral movement with respect to the axis of the catheter. A friction layer within the interior of the band is applied to prevent longitudinal movement along the axis of the catheter. In U.S. Pat. No. 4,165,748, the catheter is secured within a foldable center member, which prevents longitudinal movement. Adhesive is used on the interior surface of the foldable member to prevent axial movement. However, the catheter can only be removed by removing the entire holder so that it is not releasably secured.

In general, the prior art describes methods for securing tubular catheter devices to prevent movement in only one direction. Generally, adhesive or friction means are needed to prevent movement in two directions. The preventing of movement in three directions, that is longitudinally (axially), laterally and vertically is desirable, and has not been effectively achieved.

Complex devices, such as pressure monitor devices, are attached to very sensitive transducers and electronic monitoring devices capable of measuring for example, arterial and pulmonary pressure to within a high degree of accuracy. Such pressure monitor devices are prone to bubbles being lodged therein. The bubbles must be removed from the device in order to prevent interference with the pressure monitoring. In sophisticated pressure monitor devices, it is imperative that the bubbles be dislodged and vented. To do this effectively, the pressure monitor device must be removed from the patient. This increases the incidents of removing the device from the patient and retaping device to the patient. Given the sensitivity of such devices, proper orientation is very important and they must be readily attached and reattached in a suitable position, level with the heart, and so as to prevent movement in all three direction.

Pressure monitor devices are used in connection with a Swan-Gantz or pulmonary artery catheter or arterial line catheter to assess the condition of patients in serious cardiovascular distress. The Swan-Gantz or pulmonary artery catheter is fed through to a patient's pulmonary artery via the subclavian or jugular vein to directly monitor the pressure at one or more points. In order to obtain an accurate pressure reading, a balloon at the end of the catheter is inflated to block the force of back pressure so that the catheter will only be exposed to the static (systolic) pressure within the artery. The systolic static pressure is the pressure exerted by the blood on the vessels, as a result of the force created by the contraction of the heart. One end of the catheter is inserted into the pulmonary artery for pulmonary artery pressure or inserted into the radial artery to monitor blood pressure, and the other end is attached to the pressure monitor device. The pressure monitor device is connected to a transducer which converts the force of the pressure signal to an electronic signal which may then be recorded on, for example, a chart monitor. The Swan-Gantz catheter and pressure monitor are used, for example, to assess cardiovascular and pulmonary function, assess left ventricular function, and to assess fluid status and cardiac output. These assessments are generally done for patients who are in a critical condition such as, left ventricle failure, cardiogenic shock, myocardio infraction (heart attack), hypovolemia (inadequate blood volume), complex circulatory situations (for example, acute burns) and in medical emergencies.

Generally, a pressure monitor device serves a number of functions, it (1) provides a connection to the Swan-Gantz catheter; (2) supports a transducer to monitor the patient's blood pressure; (3) provides a connection for feeding solution from an infusion line and through the catheter; and (4) provides a port for obtaining patient fluid samples. During the time it is desired to monitor the blood or pulmonary pressure, flow from the infusion line is terminated and a three way valve is turned which provides communication between the transducer and the catheter. When a fluid sample is taken, the three way valve is again turned to terminate flow from the infusion line and to permit communication between the catheter and a sampling or vent port.

It is extremely important to frequently and accurately monitor systolic blood or pulmonary artery pressure or both. To do this a pressure monitor device such as the Critaflo, manufactured by Spectramed is connected between the catheter and a transducer. The transducer is connected to a cardiac monitor which provides a visual display, or reading. When using for pulmonary artery readings it is extremely important to secure the device at the patient's phlebostatic axis mid axillary line, or the reading will be altered. During such use it is important to secure the device and prevent its movement longitudinally, vertically and laterally. Readings could be affected by such movement. In particular, vertical movement must be prevented because the elevation of the transducer must be equal to the elevation of the point at which the catheter is exposed to systolic pressure. The systolic pressure is merely a static pressure exerted by the column of blood, therefore, the elevation of the column of blood, in relation to the elevation of the transducer is important. It is also desirable to have constant contact between the transducer and the blood within the pressure monitor device. Therefore, the monitor device should not be tilted vertically. Periodically and sometimes frequently, bubbles may collect in the dome or chamber of the pressure monitor. The bubbles must be removed because the bubbles can interfere with the sensing of the pressure force by the transducer and dampen the pulmonary artery or arterial wave form. This interference will distort the visual wave form readings. Bubbles will also affect the numerical or mean values of the systolic, diasystolic blood and pulmonary pressure readings. Therefore, it is important to flush the dome or chamber of the pressure monitor device before using it, and to regularly dislodge and discharge bubbles from within the dome or chamber during use.

Air may enter the pressure monitor device from the infusion solution bag when the bag is inverted or when the supply of infusion solution is exhausted. This is one of the reasons why bubbles occur in the pressure monitor device. It is often necessary to remove the device in order to effectively manipulate it to dislodge and discharge bubbles. It is this removal and retaping which is source of irritation to the patient's skin. Such irritations include tape burns and blisters.

In the specific example of the Critaflo pressure monitor device, it consists of essentially three branches, one branch is supported on a beam carried by a flat bottom member. The other two cantilever branches are unsupported. This produces a relatively unstable cantilever projection. The flat bottom has two parallel and opposed side slots. Tape is threaded through the slot, on one side, and under the bottom and through the slot on the other side, and around the patient's forearm, or mid axial line to secure the device. Securing the bottom portion, only, in this manner, does not effectively prevent longitudinal movement. Many times it does not stick and basically comes off. The pressure monitor device is then found on the floor. Obviously, this affects readings. It also poses a hazard to the patient if the entire catheter becomes dislodged. It less effectively prevents lateral and vertical movement, particularly of the cantilevered branches. The tape must be totally removed to release the device to discharge the bubbles. This periodic taping and retaping, causes severe skin irritation and excessive costs for tape and for the labor of medical personnel to periodically retape, as frequently as every hour.

In order to provide releasable securing means effective in more than one plane of movement and to also provide the advantages of releasably securing the device so it can be repeatedly applied and removed, and which is cost effective, I have devised a new support fastening system.

As far as I am aware, the prior art has not been directed to the problem of securing pressure monitor devices currently in use which are more complex then the simple tubular catheters used in the past. Such complex devices must be secured in the lateral (horizontal), vertical and longitudinal (axial) directions in order to work effectively with the advanced pulmonary and arterial monitoring systems.

Thus, currently, in order to provide the advantage of preventing movement in one or more directions, adhesive bandaging material is utilized where the bandage completely encircles the limb of the patient to which the pressure monitor device or similar device is to be secured. A significant excess of adhesive bandaging is used to provide a wide base of support. This is time consuming, expensive and difficult for medical personnel, with the frequency of effectively flushing air bubbles from the pressure monitor device. It is very uncomfortable for the patient since the tape must be removed and reapplied each time and in the same general area as the original tape which then, after a number of applications and removals, may cause extreme pain and discomfort to the patient. Also, medical personnel may not reapply the device in exactly the same position, which may affect the accuracy of devices connected to today's pressure monitor devices and the systems with which they are used. It is of extreme importance that the pressure monitor device be secured at a level of the heart known as the phlebostatic axis or mid-axillary line.

Among the objectives of the present invention are to provide a method and an apparatus for releasably securing a pressure monitor device such as, the Critaflo, or a similar device to prevent its movement in the axial, lateral and vertical directions while in use; to provide a desired orientation of a pressure monitor device or similar device with respect to the level at which the pressure is to be monitored; to improve the accuracy of pressure monitoring by preventing movement of the device in more than one direction and; to provide a quick and easy method for releasing the device to manipulate it to discharge bubbles which interfere with pressure monitoring. Another objective is to facilitate the alignment of the device when attaching or reattaching the device by providing a guide for the user.

In accordance with the invention there is provided a fastening system for releasably securing a pressure monitor device or similar branched device to a patient. The apparatus generally consists of an adhesive sheet constructed and arranged to engage the base of the device, carry the device and at least one strap which folds over and releasably secures said device to said sheet and a releasable fastener which releasably secures the base of said device.

BRIEF DESCRIPTION OF THE DRAWINGS

FIG. 1 is a diagrammatic view showing the apparatus as applied to a patient having a catheter monitor device, attached at the chest along the patient's mid-axial line.

FIG. 2 is a fragmentary plan view, on enlarged scale, showing the apparatus as applied to a patient having a catheter monitor device attached at the arm.

FIG. 3 is a top plan view showing the apparatus securing a catheter monitor device. 20 FIG. 4 is a sectional view taken generally along 4—4 FIG. 3.

FIG. 5 is a front elevational view of the apparatus securing a catheter monitor device.

DETAILED DESCRIPTION OF THE INVENTION

Referring to FIG. 1, a typical system 12 to which the invention relates, includes a pressurized infusion bottle 14 which feeds infusion solution through an infusion line 16 to and through a pressure monitor device 18 at the patient's mid-axial line and through a catheter line 20 to the patient's chest 22 and to the heart (not shown) to monitor pulmonary artery pressure. Blood pressure readings 24 are recorded on monitor 26 which is connected through a transducer line 28 to pressure monitor device 18. As shown in FIG. 2, pressure monitor device 18 is secured by a fastening system 30 for monitoring through catheter line 20 which enters the patient's body through the forearm 32 to monitor blood pressure via the radial artery.

Pressure monitor device 18 consists of generally three branches. A first branch 34 provides communication between transducer line 28 and catheter line 20. As shown in FIG. 3, transducer line 28 is connected to a transducer 38. Transducer 38 is connected to a connector cap 36 which houses a diaphragm 40 which communicates with a chamber 42. Chamber 42 communicates with a conduit 44 through a valve 46 and through a conduit 48 and a connector 50 to the catheter line 20 which terminates at the heart or an artery within the patient 10.

A three way valve 46 permits flow through the branch 34 when a stem 52 is positioned 90° from the position shown in FIG. 3 and parallel to a conduit 54. A second branch 56 permits flow from infusion line 16 to chamber 42. Infusion line 16 is connected to a cylinder 58 which contains a plunger 60. Cylinder 58 and plunger 60 communicate with chamber 42 and when a lever 62 of plunger 60 is activated, any bubbles in chamber 42 will be dislodged and will be discharged through a vent port 64. As shown in FIG. 5, cylinder 58 is supported on two support beams 59, which are carried by a base 61. A third branch 66 permits access to patient fluid at valve 46 through conduit 54 and vent port 64. Fluid samples may be taken through vent port 64 when stem 52 is rotated 180° from the position shown in FIG. 3, thereby providing communication between conduit 48 and conduit 54 through valve 46. During the time infusion takes place and during the time pressure readings are taken, stem 52 is turned 90° from the position shown in FIG. 3 so that it is parallel to conduit 54.

The fastening system 30 consists of a flexible adhesive sheet 68, which is preferably a silk tape. The adhesive sheet 68 provides a wide, and secure foundation for securing pressure monitor device 18.

Adhesive sheet 68 has a pressure sensitive layer 69 applied to its bottom side 70 which is exposed when a protective peelback sheet 71 is removed. A top side 72 of sheet 68 is a cloth-like material. The adhesive sheet 68 is applied to the patient's chest 22 or forearm 32. Adhesive sheet 68 provides a base to carry one or more securing straps 74, which have one end 76 permanently secured to adhesive sheet 68. The other end 78 of the strap 74 is releasably secured to adhesive sheet 68 by means of releasable fasteners 80.

In order to secure the Critaflo pressure monitor device 18 to adhesive sheet 68, a securing strap 74, as shown in FIG. 4, is folded over the first branch 34 of the device 18. Preferably, there are two securing straps 74 one on either side of valve 46, folded over conduit 44 and 48 respectively. The releasable fastener 80 on one end of each strap is then secured in place.

The releasable fastener 80 is used to secure a base 61 which supports beams 59 which carry a branch of the device 18. The releasable fastener 80 consists of two mating elements 82a and 82b, one of which is bonded to the top side of sheet 68 as by an adhesive, and the other of which is similarly bonded to the base 61 of the device 18.

The releasable fasteners 80 include two mating elements 82a and 82b. One element 82a is a loop pile element 82a and the other element 82b is a hook element 82b constructed and arranged to releasably engage the loop pile element 82a. Preferably, the loop pile element 82a has a plurality of fibers interlocked to define a needle punch loop material and the hook element 82b has a plurality of closely spaced hooks. The releasably engaging hook and pile elements 82a and 82b are sold under the trademark Velcro.

It should be appreciated that as shown in FIGS. 3 and 5, the folding over of straps 74 and the securing of the straps 74 with releasable fasteners 80 prevents movement of device 18 without interfering with the rotation of stem 52 on valve 46. The releasable securing of base 61 with fasteners 80 does not interfere with operation of lever 62 and this method is not encumbered by beams 59 on base 61.

Preferably, adhesive sheet 68 has a line 75 on its top side 72 which aligns with the axis of branch 34 of the pressure monitor device 18, to facilitate alignment of the device 18, when it is attached or reattached. The line 75 is preferably a blue line parallel to branch 34 which contains the transducer. When applied, adhesive sheet 68 is level with the transducer port and at a level with the mid-axial line of the patient.

The device 18 is thereby releasably secured from movement in any direction. The device may easily and quickly be removed and reapplied and may be accurately aligned when reapplied. The incidents of removing and reattaching are essentially unlimited, and there is no irritation to the patient's skin.

It should be appreciated that the fastening system disclosed is useful for attaching a variety of similar branched devices to a patient. It also provides a means for more effectively securing a traditional tubular catheter device. It should be understood that many modifications and variations are possible in light of the above teachings and the present invention may be practiced otherwise than as specifically described.

I claim:

1. A fastening system for removably securing a pressure monitoring device to a patient wherein said pressure monitoring device comprising a base,
   a first branch carried by said base adapted to provide communication to a catheter line;
   a valve in said first branch,
   a second branch communicating with said first branch through said valve and adapted to communicate with a transducer line on one side of said valve, said system comprising:
   a flexible sheet forming a wide area of support constructed and arranged to carry the device, said sheet comprising a top side, a bottom side and two pairs of opposite edges, said top side of said sheet comprising a cloth-like material and said bottom side of said sheet comprising a pressure sensitive adhesive thereon for applying said sheet to the patient;

a pair of straps each of which has two ends, one end of each said strap being permanently secured to the top side of said sheet along one edge of said sheet, releasably fastener means releasably securing the other end of each said strap to the top side of said sheet at an opposite edge, each said releasable fastener means comprising a pair of mating elements, one of said elements of each pair being secured to the top side of said adhesive sheet and the other element of each pair being secured to the other end of a respective strap, said mating elements of each releasable fastener means being releasably interengageable, one of said straps being adapted to be folded over said first branch of the pressure monitoring device on one side of the valve of the pressure monitoring device and the other of said straps being adapted to be folded over the second branch on the other side of said valve of the pressure monitoring device, additional fastener means comprising a pair of mating elements, one of said elements adapted to be secured to an underside of the base of the pressure monitoring device and the other mating element being secured to the top side of said sheet for releasably securing the base to said sheet.

2. A fastening system according to claim 1 wherein said pair of mating elements of said releasable fastener means comprises a first element with one side which has the pressure sensitive adhesive and with another side which has a loop pile element, and a second element with one side which has the pressure sensitive adhesive and another side which has a hook element constructed and arranged to releasably engage said loop pile element.

3. The fastening system of claim 2 wherein said loop pile element includes a plurality of fibers interlocked to define a needle punch loop material and said hook element includes a plurality of closely spaced hooks which can be utilized to releasably engage said loop pile element.

4. A fastening system according to claim 1 including said pressure monitoring device, said valve comprising a three-way valve, and said two straps being spaced apart and folded over each respective one of said two branches transverse thereto on either side of said valve and releasably securing said device to the top of said adhesive sheet by said respective releasable fasteners.

5. The fastening system as in claim 4 wherein said pressure monitoring device includes a third branch extending from said second branch and having a vent port said three way valve being provided between said catheter line, said transducer line and said vent port and connected thereto by respective conduits, said fastening system comprising said pressure monitoring device with said first and second branches being carried by the base and said two straps being spaced apart and folded over said first branch transverse thereto and on either side of said valve and parallel to said second and third branches releasably securing said device to the top side of said adhesive sheet by said respective releasably fasteners.

* * * * *